United States Patent [19]
Goldin et al.

[11] Patent Number: 5,137,449
[45] Date of Patent: * Aug. 11, 1992

[54] INTRAORAL MEDICATION RELEASING SYSTEM

[75] Inventors: Bruce Goldin; Ronald J. Billings, both of Rochester, N.Y.; Tibor Sipos, Lebanon; Bruce E. Kohut, Colts Neck, both of N.J.; Kathleen Woodward, San Diego, Calif.

[73] Assignees: Johnson & Johnson Consumer Products, Inc., N.J.; Eastman Dental Center, N.Y.

[*] Notice: The portion of the term of this patent subsequent to Sep. 17, 2008 has been disclaimed.

[21] Appl. No.: 360,674

[22] Filed: Jun. 2, 1989

Related U.S. Application Data

[63] Continuation-in-part of Ser. No. 325,815, Mar. 20, 1989, Pat. No. 5,049,077.

[51] Int. Cl.⁵ .......................................... A61C 19/06
[52] U.S. Cl. ...................................... 433/229; 433/80; 433/215
[58] Field of Search .................. 433/80, 215, 229, 23; 604/77; 424/435

[56] References Cited

U.S. PATENT DOCUMENTS

| | | | |
|---|---|---|---|
| 589,712 | 9/1897 | Fouquier | 604/77 |
| 1,622,616 | 3/1927 | Temple | 433/215 |
| 1,642,653 | 9/1927 | Goldstein | 433/215 |
| 1,934,688 | 11/1933 | Ackerman | 604/77 |
| 2,835,628 | 5/1958 | Saffir | 433/229 |
| 3,421,221 | 1/1969 | Silverman et al. | 433/23 |
| 3,527,218 | 9/1970 | Westline | 128/229 |
| 3,600,807 | 8/1971 | Sipos | 433/229 |
| 3,624,909 | 12/1971 | Greenberg | 433/80 |
| 3,688,406 | 9/1972 | Porter et al. | 433/80 |
| 4,020,558 | 5/1977 | Cournut et al. | 433/80 |
| 4,021,921 | 5/1977 | Detaille | 433/80 |
| 4,106,501 | 8/1978 | Ozbey et al. | 128/62 |
| 4,175,326 | 11/1979 | Goodson | 433/80 |
| 4,412,825 | 11/1983 | Tokarz | 433/229 |
| 4,464,114 | 8/1984 | Anthony | 433/229 |
| 4,465,462 | 8/1984 | Ticknor | 433/136 |
| 4,523,910 | 6/1985 | Makovich | 433/80 |
| 4,560,351 | 12/1985 | Osborne | 433/80 |
| 4,671,768 | 6/1987 | Ton | 433/174 |
| 4,681,544 | 7/1987 | Anthony | 433/215 |
| 4,685,883 | 8/1987 | Jernberg | 433/215 |
| 4,741,700 | 5/1988 | Barabe | 433/229 |
| 4,861,268 | 8/1989 | Garay et al. | 433/229 |
| 4,892,483 | 1/1990 | Douglas Jr. | 433/215 |

FOREIGN PATENT DOCUMENTS 3626692  3/1988  Fed. Rep. of Germany.

OTHER PUBLICATIONS

Hanes et al., "Effective Delivery Systems for Prolonged Fluoride Release: Review of Literature", JADA, vol. 113, pp. 431–436, Sep. 1986.
Mirth, "Controlled-Release Therapeutic Systems: Technology Applicable to the Treatment of Oral Disease", Adv. Dent. Res. 1, pp. 109–118, Oct., 1987.
Cowsar, "Introduction to Controlled Release", Research Paper, pp. 1–13.

Primary Examiner—John J. Wilson
Attorney, Agent, or Firm—Paul A. Coletti

[57] ABSTRACT

A system for long term releasing of medication in the mouth, and especially an intra-oral fluoride releasing system (IFRS) for releasing fluoride over a long term for inhibiting the formation of caries in the teeth. The system uses a holder for retaining and protecting intraoral fluoride tablets or other intra-oral medicament in the form of fluoride releasing devices (IFRD). The holder has a plate with retaining sides and retaining posts or a carrier. The tablet will fit within the holder. The tablet may be located in the carrier, or ligature bands can be tied around the tablet in order to releasably hold the IFRD within the holder. The system causes a level of fluoride to be maintained over a long term within the mouth which has been found chemically effective for caries control and without causing severe irritation to oral tissues.

7 Claims, 4 Drawing Sheets

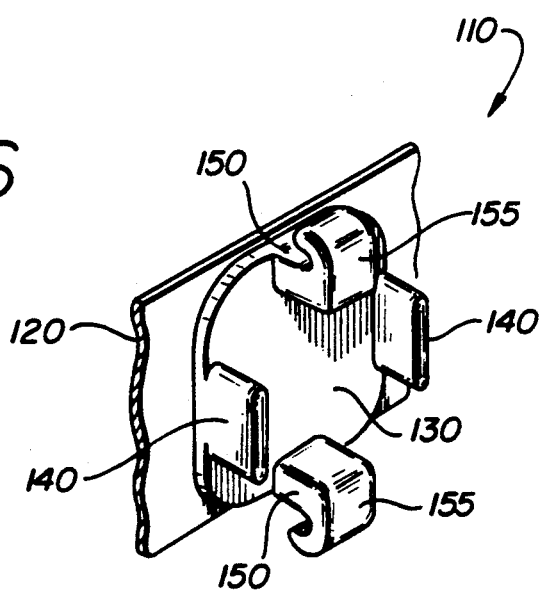
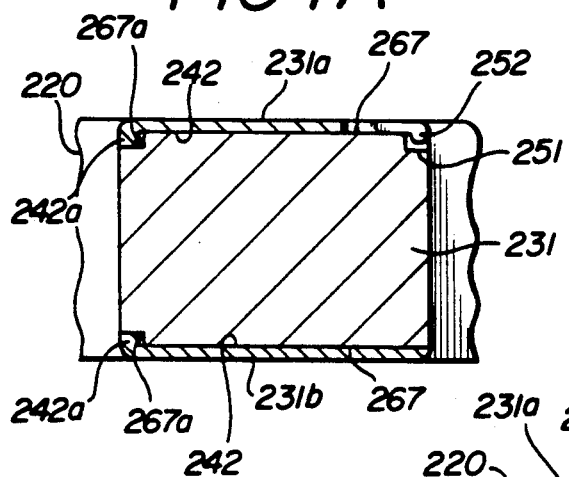
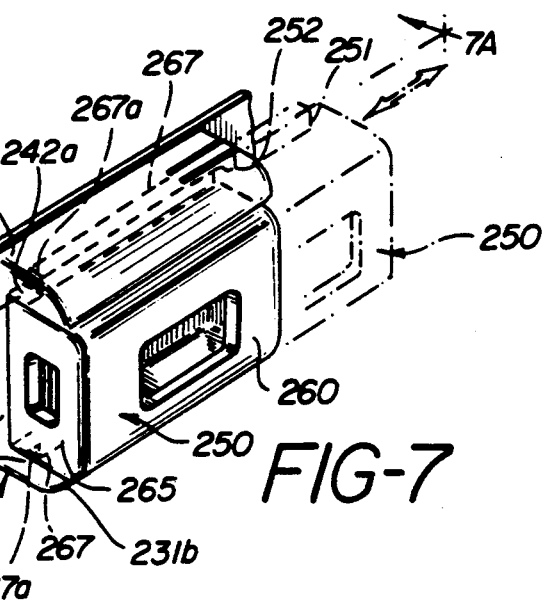
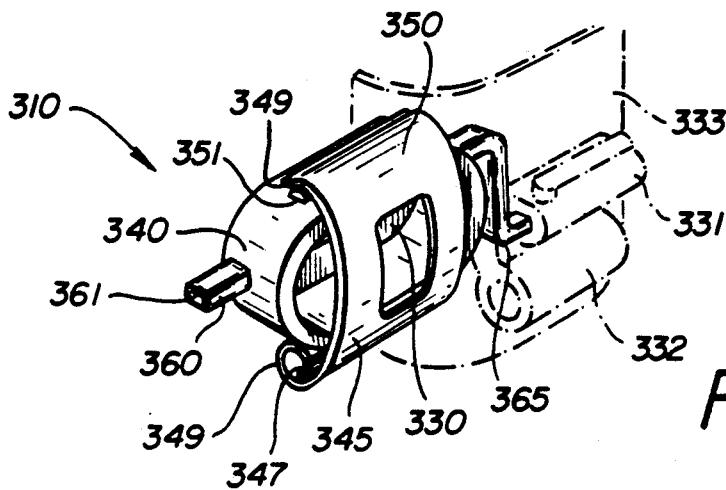

INTRAORAL MEDICATION RELEASING SYSTEM

Parts of this invention were conceived during performance of a contract between The Eastman Dental Center and the National Institute of Dental Research Contract No. N01-DE-72571.

This application is a continuation-in-part of application Ser. No. 325,815, filed on Mar. 20, 1989, now U.S. Pat. No. 5,049,077.

FIELD OF THE INVENTION

This invention relates generally to systems for retaining and dispensing caries preventative media (fluoride) intraorally for sustained-controlled release to the teeth by the saliva over a long period of time (weeks or months) and to holders for use within the mouth which retain and protect an intra-oral fluoride-releasing device (IFRD). The combination of an IFRD and its holder comprises an intra-oral flouride-releasing system (IFRS). This invention is generally useful in intra-oral medication holders for long term timed release tablets of medication in the mouth without significant irritation of oral tissue.

BACKGROUND OF THE INVENTION

Dental research has had remarkable success in dental caries prevention. Specifically, it has been found that roughly fifty percent of children ages six through seventeen living in the United States are caries free. This remarkable progress during the last twenty years is due, in part, to better oral hygiene, use of fluoridated water, and fluoridated products, i.e., dentifrices.

Nevertheless, there are patients who remain susceptible to dental caries. For instance, twenty percent of all children account for roughly sixty Percent of all carious lesions. Also, certain subjects with diminished salivary functions are especially prone to caries, because they produce limited amounts of saliva. Other risk factors, such as poor oral hygiene, physical or mental handicaps, and certain systemic diseases or disorders may also predispose individuals to dental caries.

Recent studies have demonstrated that elevated concentrations of fluoride in the mouth for extended periods will help reduce caries. A source of such fluoride is contained in controlled-release fluoride tablets which have been called intra-oral fluoride releasing devices (IFRD's). These IFRD's release fluoride into the oral cavity for extended periods up to six months to enhance prevention of dental caries.

Previous attempts to retain IFRD's in the mouth have failed for a variety of reasons. For instance, IFRD's produced by Southern Research Institute were designed to be bonded directly to the teeth. These IFRD's were found susceptible to debonding from masticatory forces or were subject to excessive wear caused by abrasives contained in toothpastes. What is desirable, therefore, is a system whereby IFRD tablets can be safely secured and retained in the mouth until their fluoride supply is exhausted.

In addition, it is desirable to have a system (an intra-oral fluoride release system or IFRS) whereby the tablets can be replaced periodically following depletion of their fluoride content. It is further desirable for these systems to be broadly useful for children undergoing active orthodontic treatment. In general these children have an increased risk to caries development because they are not able to adequately brush their teeth. It is also desirable to provide an IFRS which does not cause severe irritation to mouth tissues What is meant by severe irritation is ulceration or acute inflammation which interferes with oral function and nutrition, such as pain, induration or necrosis or purulent exudate from tissue in the vicinity of the IFRS.

SUMMARY OF THE INVENTION

Accordingly, it is the principal object of this invention to provide an IFRS whereby the foregoing problems and needs are resolved and more particularly to provide intra-oral IFRD holders which can be safely placed and securely retained in the mouth for an indefinite period.

Briefly described, a system according to the invention comprises a holder which has a retaining member, such as a plate or band with a back surface adapted to be disposed on a surface of a tooth. This back surface is connected to a pair of opposed retaining sides within which the tablet can be placed, either directly on the plate, or in a carrier releasably connected to the plate. At the ends of the opposed retaining sides are a pair of retaining posts. These posts can be wrapped with ligatures, which extend over the tablet so that the tablet is exposed in the mouth but remains in place within the holder. An openable cover may be mounted on and extend across the retaining side. Fluoride is delivered to the oral cavity by the IFRD tablets at therapeutic levels continuing for up to six months. The IFRD can be replaced by removing and replacing the ligatures or opening the cover, removing and reinserting the carrier with a fresh tablet, or replacing the system (the IFRD and the holder) in its entirety.

These and other objects and embodiments of the invention will be better understood with the attached figures and detailed description of the drawings, in which:

DETAILED DESCRIPTION OF THE DRAWINGS

FIG. 6 is a perspective view of another embodiment of the retaining member;

FIG. 7, 7B and 7C are perspective views of variations of a second embodiment in accordance with the present invention;

FIG. 7A is a cross-sectional view across lines 7—7 of the embodiment shown in FIG. 7;

FIG. 8 is a perspective view of a third embodiment in accordance with the present invention.

DETAILED DESCRIPTION OF THE INVENTION

Figure 1:
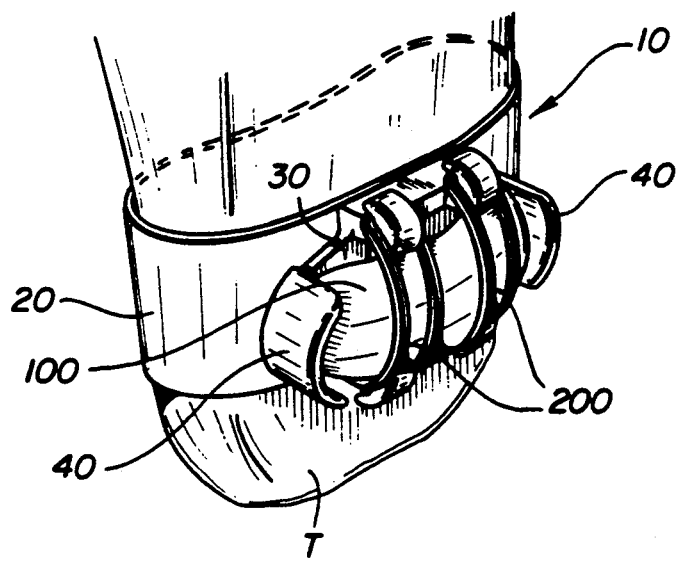
FIG. 1 is a perspective view of a first embodiment in accordance with the invention shown attached to a tooth.
Figure 2:
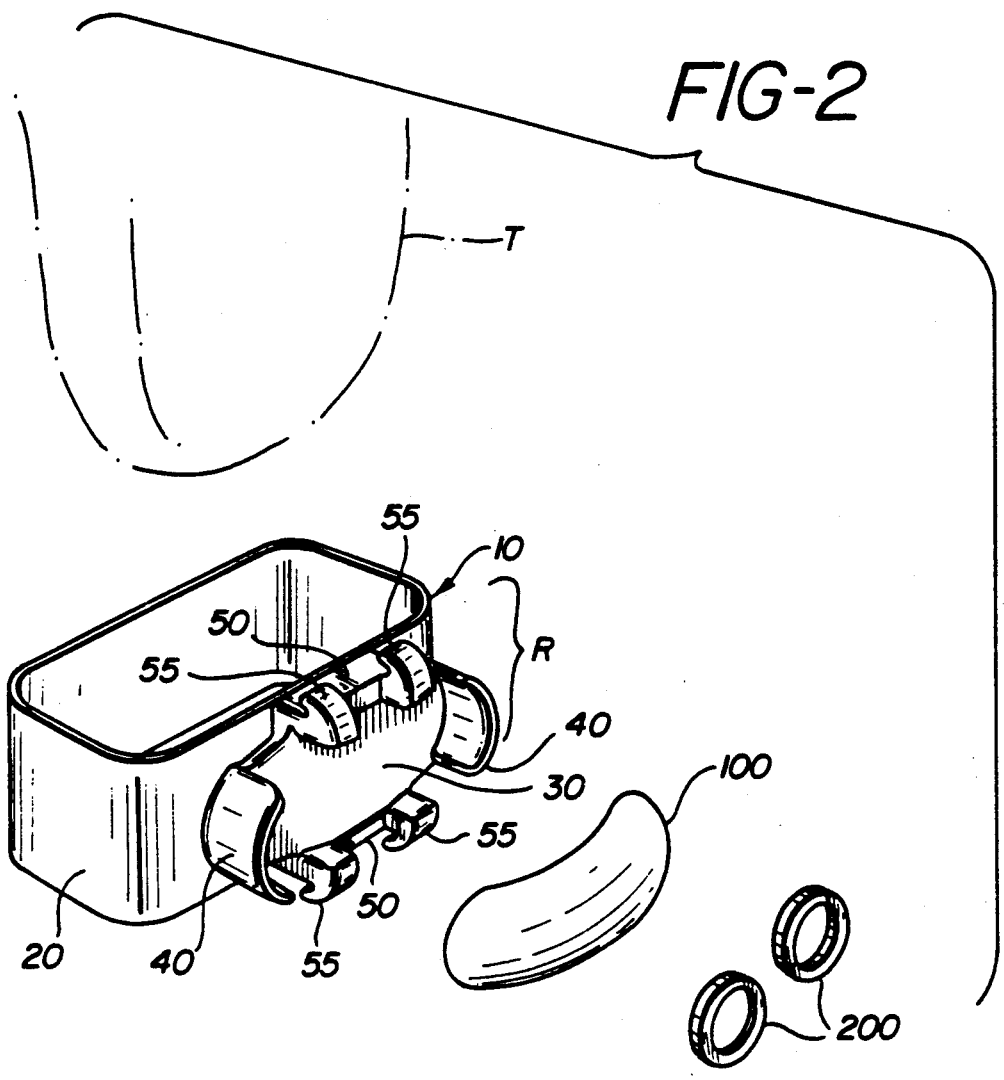
FIG. 2 is an exploded perspective view of the embodiment of the invention shown in FIG. 1 fluoride tablet.
Figure 3:
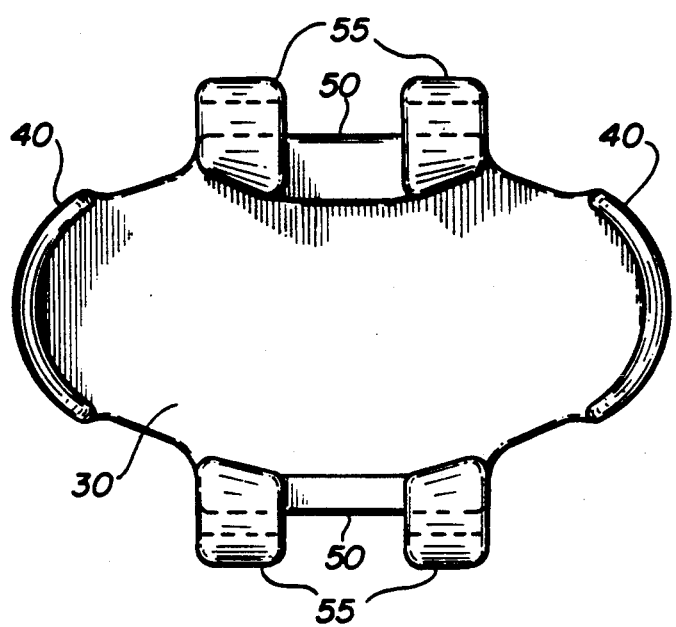
FIG. 3 is a top view of the retaining member of the holder of the embodiment of the invention shown in FIG. 1.
Figure 4:
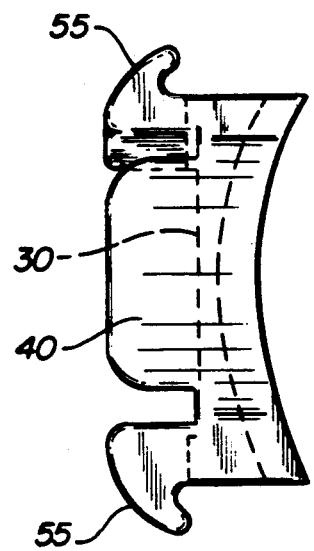
FIG. 4 is a side view of the retaining member shown in FIG. 3.
Figure 5:
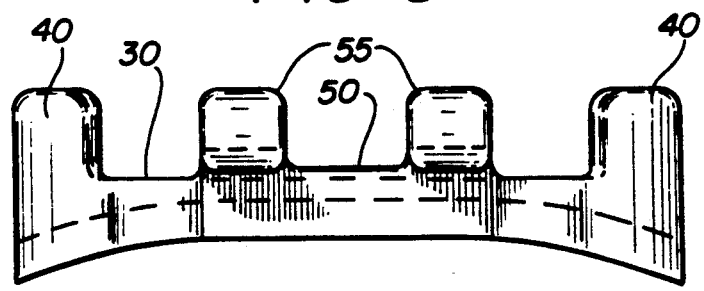
FIG. 5 is a front view of the retaining member shown in FIG. 3.

As seen from FIGS. 1, 2, 3, 4 and 5, there is provided in accordance with a first embodiment of the present invention, an IFRS having a holder 10 for tablets which will be emplaced in the mouth. These tablets are generally controlled release fluoride tablets and are oval or kidney bean shaped such as tablet 100 as seen in FIG. 2. The holder 10 is generally comprised of a band 20 which wraps around the tooth and a retaining member R. This retaining member R will generally be formed of a plate 30 having back surface which is attached, as by spot welding, to the band 20. The member R has retaining sides 40, as best seen in FIGS. 2 and 3. The tablet 100 generally fits snugly within the retaining sides 40 and against the anterior surface of the holder 10. The posterior surface of the plate may be cusp shaped to conform to the outer surface of the tooth.

In order to secure the attachment of the tablet 100 to the holder 10, the plate 30 has a pair of retaining posts 50. These posts 50 have knob-like projections 55, usually with indentations around which miniature elastic bands, known as ligature bands 200, can be attached. When the tablet 100 is inserted into the holder 10, the ligature bands 200 are placed around the knobs 55 so that they snugly hold the tablet 100 within the holder 10, as seen best in FIG. 1. The band 20 then is generally applied around the tooth. Instead of ligature bands, stainless steel ligature wires may be used, and the term ligatures or ligature bands should be taken as encompassing both endless bands and wires.

The method of application will proceed as follows: The tooth generally will have separators placed into the interdental spaces to gain dental ligament space so as to insert the band 20. The band 20 is then inserted around the tooth and made to fit snugly. The tablet 100 is placed onto the plate 30 of the holder 10. The ligature bands 200 are placed around the retaining post knobs 55 and allow the tablet to be releasably retained and protected in the mouth. As can be appreciated, if the intra-oral fluoride tablet 100 is broken in the mouth or releases its fluoride content, the ligature bands 200 can be removed, and a new tablet 100 can be inserted into the holder 10. In this way, the holder 10 can achieve any necessary permanence in the mouth dependent upon the desired dental procedure.

Another holder 10 having a retaining member 130 on a band 120 can be seen in FIG. 6. While the retaining member 30 disclosed in FIGS. 1-5 is generally oval to accommodate an oval shaped tablet, the member 130 in FIG. 6 is generally rectangular. This will hold in place a generally rectangular tablet. As can be seen, the band 120 has attached to it the back surface of the base plate of the retaining member 130. This holder 130 has two retaining sides 140 and two retaining posts 150. The pair of retaining posts is disposed between the two retaining sides 140. On each retaining post 150 there are knobs 155, around which can fit ligature bands 200, as in FIGS. 1-5. Thus, a rectangular shaped tablet is placed against the base plate of the member 130 and between its retaining sides 140. Then, the ligature bands 200 are wrapped around retaining post knobs 155. Again, the device properly remains around the tooth and hygienic treatment is possible.

As seen in FIG. 7 and FIG. 7A, there is provided a holder 210 having a band 220 which has attached to it a retaining member 230 having a plate 231 with sides 231a, 231b. The back surface of plate 231 is attached to the band 220. The plate 231 has connected to it a pair of retaining sides 231a, 231b. Each of the retaining sides 231a, 231b has a notch 242, containing a step 242a. The retaining member 230 slidably receives a drawer 250 having flanges 267 which are received within the notches 242. The step 242a in notch 242 mates with step 267a in flange 267 to keep the drawer 250 in place. This drawer 250 is generally rectangular in shape and will contain a front grill 260 and a pair of side grills 265. A detent ridge 252 on the plate 231 releasably snaps the drawer in place with step 251 in flange 267 of drawer 250 in the position shown, to prevent forward dislodgment with an extension piston.

The front and side grills 260, 265 contain sufficiently large openings so that an IFRD tablet comes into contact with the saliva in the mouth. Because the notches 242 allow the drawer 250 to slide in and out, the tablet 100 can be emplaced within the drawer 250 and then slid into the notches. The drawer 250 can be removed and a new tablet 100 can be inserted, allowing an indefinite period of reuse.

Figure 7B:
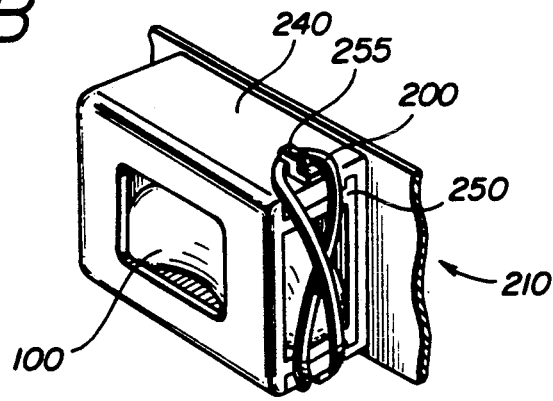

Alternately, drawer 250 can be secured by ligature bands 200 as seen in FIG. 7B. In this aspect of the present embodiment, retaining sides 240 contain retaining posts 255 much like the retaining posts 50, 150 of the earlier embodiments. After emplacement of the drawer 250 into the retaining sides 240 with a tablet 100 in place, the drawer 250 is held by ligature bands 200.

Figure 7C:
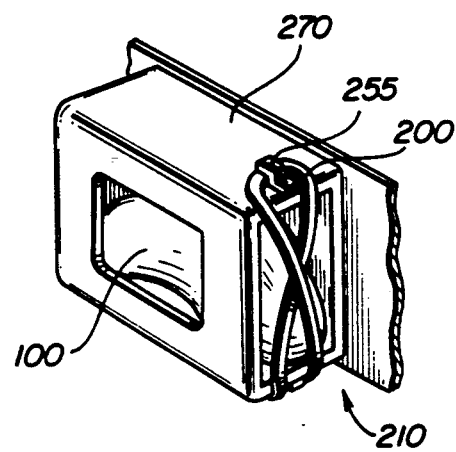

Of course, as seen in FIG. 7C, the device of the present invention can be configured so that the retaining sides and drawer form a single grill shaped retaining unit 270. This retaining unit 270 has an open side into which the tablet 100 is placed. Ligature bands 200 are then wrapped over the retaining unit opening, and securely around posts 255. Operation of the holder will be identical to the previous embodiments.

Another third embodiment of the invention can be seen in FIG. 8. This embodiment provides a holder 310 which can be used along with orthodontic dental brackets (seen as brackets 331) which are attached to a band 333. As can be seen from FIG. 8, there is an oval or rectangular shaped retaining member 330 with a cage or retaining wall 340 which generally conforms to the shape of one of the intra-oral fluoride tablets (IFRD). This retaining wall 340 has a back plate to which a post 360 is attached. An end 361 of this post extends through one side of the cage 340. The other end 365 of the post 360 is "Z" shaped, to allow an optional range of intra-oral placement. The "Z" shaped end 365 can be inserted into one of the dental brackets 331 which provides an archwire slot. Alternately, cage 340 can be attached to the tooth directly by means of adhesive. Or, the back of the base plate of the member 330 of the holder can be attached using a band as in the system as shown in FIGS. 1-7.

This holder 310 has a cover of resilient material 350 containing a grill 345. This cover has fingers 348 which curl around a rod 347, attached to the lower side of a cage 340, forming a hinge. On the cover 350 there is also a rib detent 349. This detent may catch on a projection 351 on the upper side of the cage which snugly causes the cover to attach to the cage and cover the front thereof. Thus, the cover can be opened and the tablet can be inserted within the retaining cage 340. This holder 310 can be removed and used more than one time (i.e., for other patients or moved to other brackets elsewhere in the mouth). This causes this embodiment to be versatile and may be preferred for those patients needing or having other orthodontic appliances.

Figure 9A:
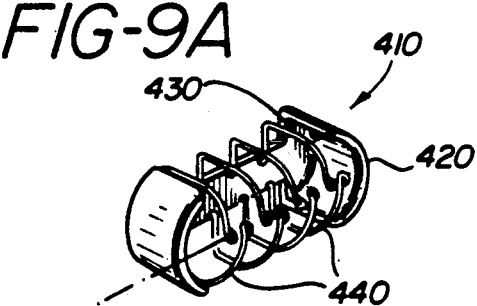
FIG. 9A, 9B, 9C are respectively a perspective and two side views of a fourth embodiment of the invention.
Figure 9B:
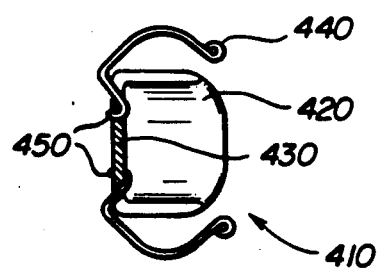
Figure 9C:
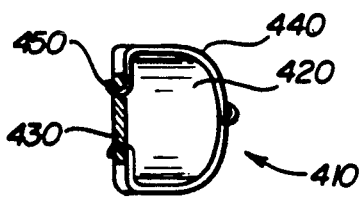

Finally, a fourth embodiment of the present invention can be seen in FIGS. 9A-9C. There is disclosed a holder 410 having a pair of side retaining walls or bands 420 which are wrapped around the tooth. Onto the band 420 is welded a back surface 430 having hinged claws 440. These claws 440 are pivoted about posts 450 to allow emplacement of the tablet 100 on the back surface 430. When in place the claws are approximated and kept closed by the wrapping of ligature bands around the claws 440. In this manner, the holder 410 adequately retains and exposes a tablet for use. Alternately, claws 440 can be connected with a longitudinal bar. If so, a spring clip as demonstrated in FIG. 8 can be used to retain the IFRD tablet in holder 410.

It should be noted that all the holder embodiments are preferably made of a high strength aluminum or other metal (e.g., stainless steel) or, in the alternative, a non-degradeable bio-compatible hardened plastic. The material withstands masticatory forces in the mouth, yet still allows large open areas of contact with the saliva to allow release of fluoride to the oral cavity.

What is claimed:

1. A system for replaceably receiving intra-oral tablets, such as intra-oral fluoride devices, comprising:
   (i) a holder having a plate with an anterior surface including means for replaceably holding individual ones of said tablets and defining a space within which said tablets are individually emplaced;
   (ii) a pair of opposed retaining sides connected to said plate, said retaining sides generally shaped to maintain said tablet on said anterior surface while permitting medication to flow from said space into the oral cavity; and
   (iii) cover means attached to said plate for removably retaining said tablet within said space and generally preventing movement of said table from said holder anterior surface, said cover means permitting medication to flow across said cover means and into said oral cavity, and wherein said cover means comprises a cover attached to one of said retaining sides at a hinge, said cover containing a pair of arms attached by a cross-arm, said cover describing an enclosed area through which medication may flow from said space into said oral cavity.

2. The system according to claim 1 wherein said holder further comprises a band fixedly attached to said plate and attachable about the body of a tooth.

3. The system according to claim 1 wherein said cover is attached to said opposite retaining side by detent means on said opposite retaining side.

4. A system for replaceably retaining and protecting an intra-oral controlled release medication tablet, such as an intra-oral fluoride device, in the mouth, comprising:

a holder having a plate for attachment on a tooth;
said tablet emplaceable upon said plate; and
said holder having retaining means connected to said plate, said retaining means comprising ak pair of retaining sides attached to said plate, and said retaining means connected to enclosing means extendable from said plate and capable of extending across said tablet and capable of generally maintaining said tablet emplaced on said plate, while also permitting medication to flow into the oral cavity,
and wherein said enclosing means comprises a cover attached to said plate at a hinge, said cover containing a pair of sides attached to said plate by a cross arm, said cover describing an enclosed area through which medication may flow into said oral cavity.

5. The system according to claim 4 wherein said retaining means has opposed retaining sides and wherein said cover is attached to said plate on one of said sides, said cover capable of holding said tablet emplaced on said plate and said retaining sides.

6. The system according to claim 5 wherein said cover is attached to said opposite retaining side by detent means on said opposite retaining side.

7. The system according to claim 4 wherein said holder further comprises a band fixedly attached to said plate and attachable about the body of a tooth.

* * * * *